United States Patent
Lin

(10) Patent No.: US 7,558,364 B2
(45) Date of Patent: Jul. 7, 2009

(54) DYNAMIC DOSE CONTROL FOR COMPUTED TOMOGRAPHY

(75) Inventor: Zhongmin Steve Lin, Solon, OH (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 278 days.

(21) Appl. No.: 10/599,418

(22) PCT Filed: Mar. 30, 2005

(86) PCT No.: PCT/IB2005/051067

§ 371 (c)(1),
(2), (4) Date: Sep. 28, 2006

(87) PCT Pub. No.: WO2005/099577

PCT Pub. Date: Oct. 27, 2005

(65) Prior Publication Data

US 2008/0232542 A1    Sep. 25, 2008

Related U.S. Application Data

(60) Provisional application No. 60/561,736, filed on Apr. 13, 2004, provisional application No. 60/599,123, filed on Aug. 5, 2004.

(51) Int. Cl.
*A61B 6/00* (2006.01)
(52) U.S. Cl. ............................................ 378/16; 378/4
(58) Field of Classification Search ............... 378/2, 378/16, 8, 15, 160
See application file for complete search history.

(56) References Cited

U.S. PATENT DOCUMENTS

| 5,867,555 | A | 2/1999 | Popescu et al. |
| 6,198,789 | B1 | 3/2001 | Dafni |
| 6,385,280 | B1 | 5/2002 | Bittl et al. |
| 7,042,977 | B2 | 5/2006 | Dafni |
| 2004/0062341 | A1 | 4/2004 | Popescu et al. |

OTHER PUBLICATIONS

Gies, M., et al.; Dose reduction in CT by anatomically adapted tube current modulation. I. Simulation studies; 1999; Med. Phys.; 26(11)2235-2247.

Kalender, W.A., et al.; Dose reduction in CT by anatomically adapted tube current modulation. II. Phantom measurements; 1999; Med. Phys.; 26(11)2248-2253.

Suess, C., et al.; Dose optimization in pediatric CT: current technology and future innovations; 2002; Pediatr. Radiol.; 32:729-734.

*Primary Examiner*—Edward J Glick
*Assistant Examiner*—Mona M Sanei

(57) ABSTRACT

In a dose modulation method, transmission tomographic imaging data of an associated imaging subject are acquired using a radiation source (14) revolving around the associated imaging subject. During the tomographic imaging, an estimated attenuation of radiation is determined for an upcoming position or angular bin (72₁, 82) of the revolving radiation source based on attenuations determined at previously acquired positions or angular bins (70₁, 84, 90) of the radiation source. Prior to acquiring tomographic imaging data at the upcoming position or angular bin, a level of radiation produced by the radiation source is adjusted based on the estimated attenuation of radiation.

12 Claims, 5 Drawing Sheets

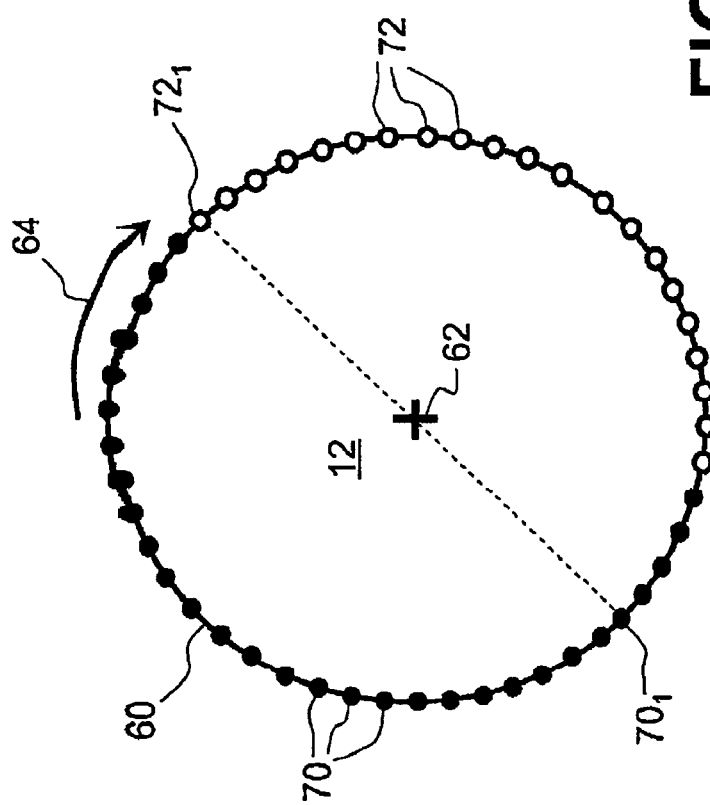

Figure 1:
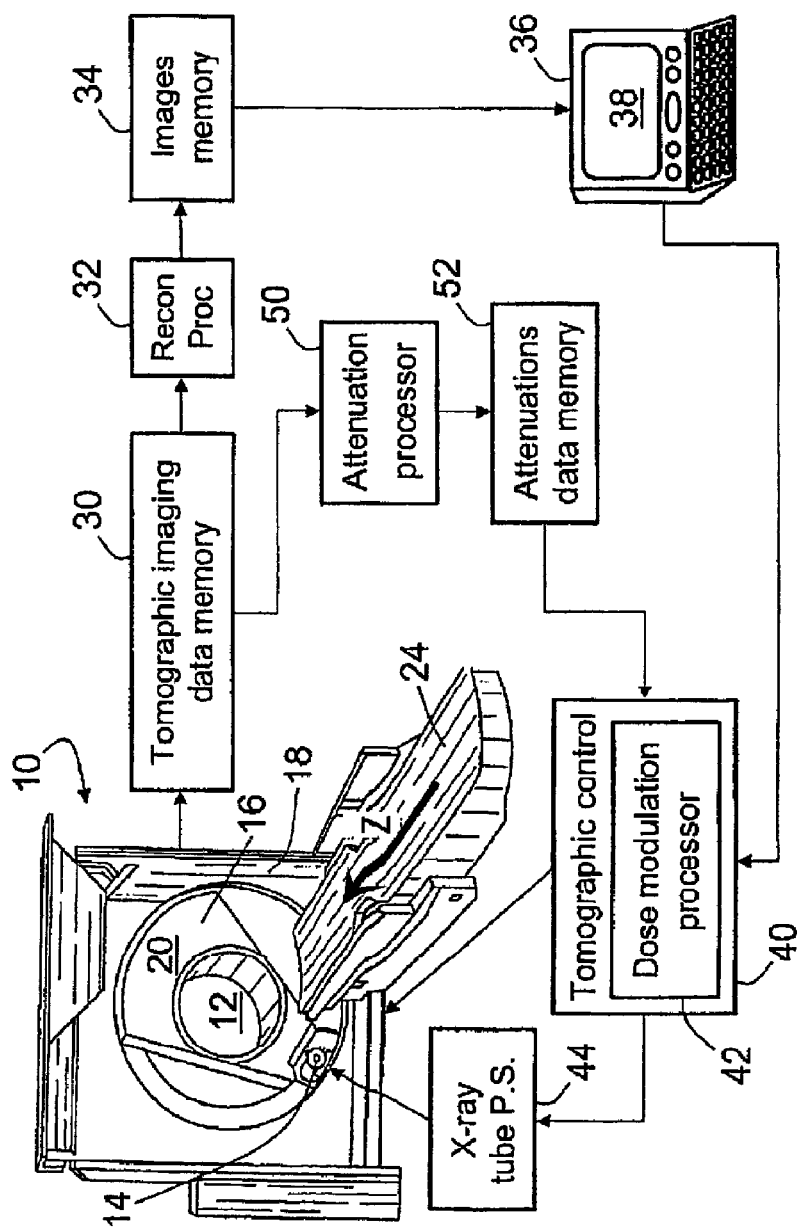

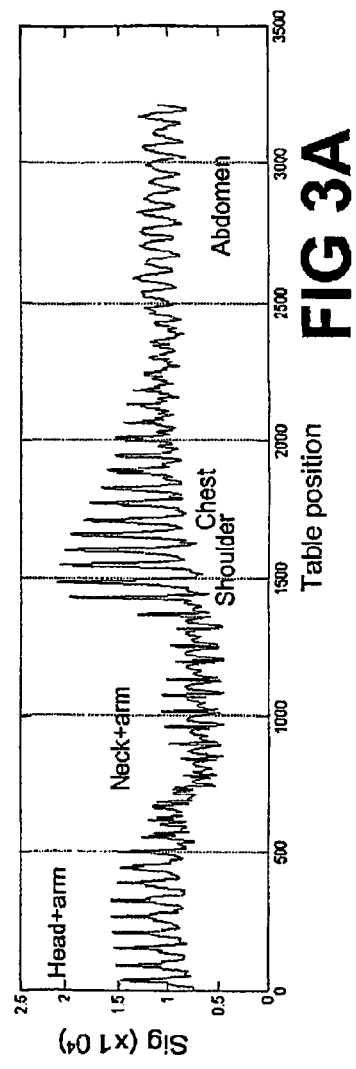
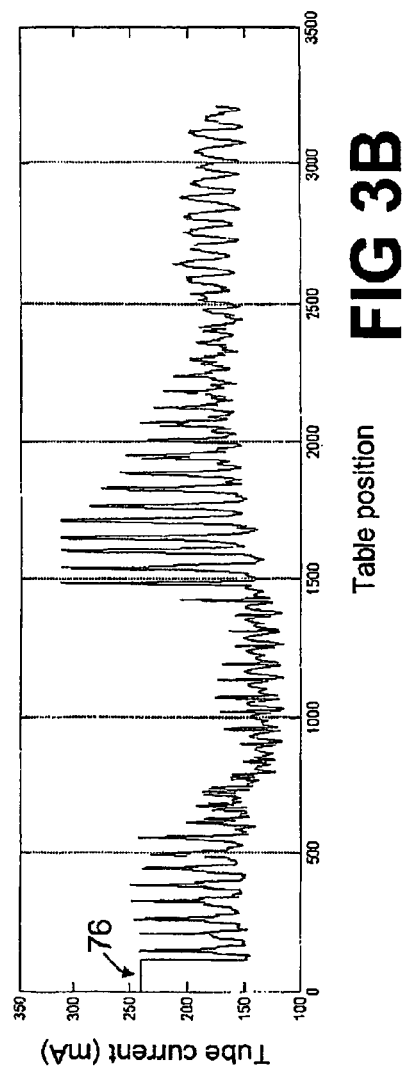

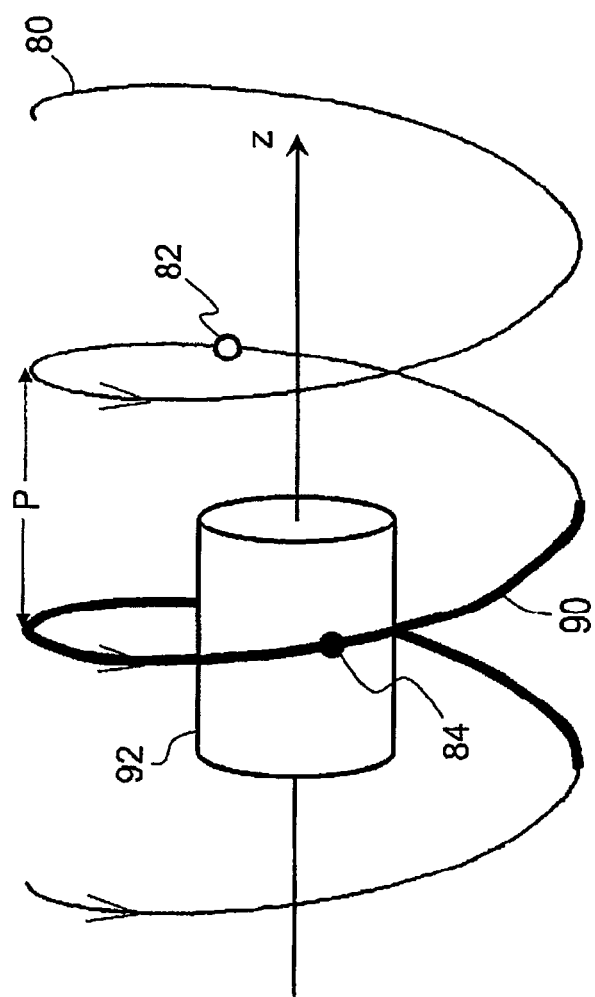

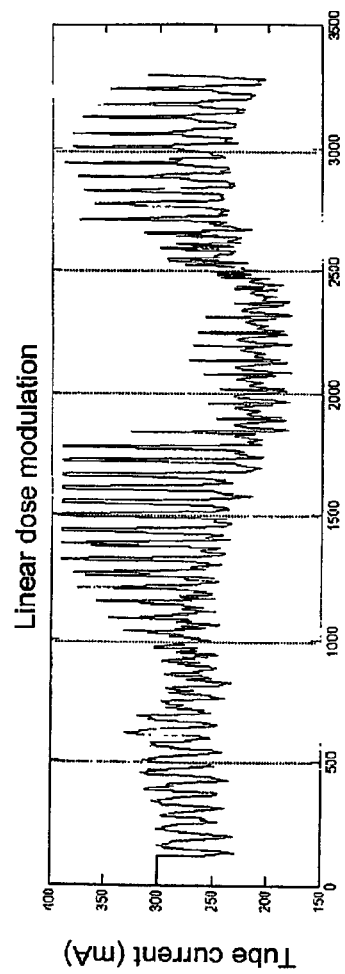
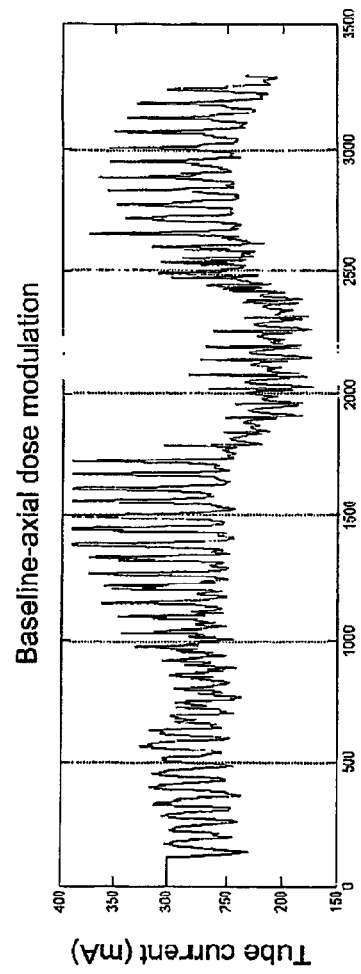

DYNAMIC DOSE CONTROL FOR COMPUTED TOMOGRAPHY

CROSS REFERENCE TO RELATED APPLICATIONS

This application claims the benefit of U.S. provisional application Ser. No. 60/561,736 filed Apr. 13, 2004 and U.S. provisional application Ser. No. 60/599,123 filed Aug. 5, 2004, both of which are incorporated herein by reference.

The following relates to the tomographic scanning arts. It finds particular application in computed tomography imaging, and will be described with particular reference thereto. However, it also finds application in transmissive radiation-based tomographic scanning generally, including tomographic radiation therapy and the like.

In transmissive radiation-based tomographic imaging, the radiation dose delivered to the imaging subject is of concern. In medical imaging, government regulatory agencies typically impose ceilings on the permissible amount of radiation exposure. For airport screening or other non-medical applications, limiting the amount of radiation exposure can reduce damage to radiation-sensitive items such as camera film, consumer electronics, and the like.

One way to limit radiation exposure is to modulate the output of the radiation source (for example, the x-ray tube in typical computed tomography imaging scanners) to reduce the applied radiation intensity based on the path length through the patient. In some dose modulation approaches, x-ray attenuation at an angular position is compared with the maximum x-ray attenuation in a revolution to obtain modulated x-ray tube current at this angular position. These dose modulation techniques are based on the attenuation ratio in a single revolution during a helical scan and achieves only axial (2D) current modulation and not suitable for conventional helical scan which produces three-dimensional image. These existing dose modulation techniques do not account for differences in imaging subject density transverse to the calibration axial slice, such as density differences in a human imaging subject between the head, neck, shoulder, chest, and abdominal regions.

Some imaging procedures employ one or more planar scout scans in which the radiation source does not revolve around the imaging subject. Planar scout scans do not provide three-dimensional density information suitable for calibrating the dose modulation during the subsequent three-dimensional tomographic imaging. For human imaging subjects, a planar scout scan can be used in conjunction with a density model of the human body to estimate the three-dimensional density characteristics of the specific human subject being imaged. However, substantial errors can arise due to variations in body shape, weight, height, and so forth. Especially when used in conjunction with tilted angle scans, the error of the estimated average attenuation may be so large as to be unusable for dose modulation.

The present invention contemplates improved apparatuses and methods that overcome the aforementioned limitations and others.

According to one aspect, a dose modulation method is provided. Transmission tomographic imaging data of an associated imaging subject are acquired using a radiation source revolving around the associated imaging subject. During the tomographic imaging, an estimated attenuation of radiation is determined for an upcoming position or angular bin of the revolving radiation source based on attenuations determined at previously acquired position is or angular bins of the radiation source. Prior to acquiring tomographic imaging data at the upcoming position or angular bin, a level of radiation produced by the radiation source is adjusted based on the estimated attenuation of radiation.

According to another aspect, a dose modulated tomographic apparatus is disclosed. A tomographic scanner acquires transmission tomographic imaging data of an associated imaging subject. The tomographic scanner includes a radiation source revolving around the associated imaging subject. A means is provided for determining an estimated attenuation of radiation for an upcoming position or angular bin of the revolving radiation source based on attenuations at previously measured positions or angular bins of the radiation source A means is provided for adjusting a level of radiation produced by the radiation source based on the estimated attenuation of radiation.

One advantage of the present invention resides in reducing patient dose.

Another advantage of the present invention resides in dynamically optimizing image quality.

Another advantage resides in elimination of scout scans in calibrating the three-dimensional dose modulation.

Another advantage resides in supporting tilted angle scans.

Another advantage resides in dose modulation that is specific to the subject presently being imaged.

Yet another advantage resides in accurately accounting for variations in imaging subject density in both the axial and z-directions.

Numerous additional advantages and benefits will become apparent to those of ordinary skill in the art upon reading the following detailed description of the preferred embodiments.

The invention may take form in various components and arrangements of components, and in various process operations and arrangements of process operations. The drawings are only for the purpose of illustrating preferred embodiments and are not to be construed as limiting the invention.

FIG. 1 shows a tomographic imaging system employing dose modulation.

FIG. 2 diagrammatically shows determination of an estimated radiation attenuation value for an upcoming radiation source position or angular bin.

FIG. 3A plots the tomographic signal that used to modulate x-ray tube current versus table position for a whole-body scan starting at the head and terminating in the abdominal region.

FIG. 3B plots the dose modulated x-ray tube current versus table position for a whole-body scan starting at the head and terminating in the abdominal region.

FIG. 4 diagrammatically shows a helical radiation source trajectory with radiation attenuation sources identified which are suitable for use in determining an estimated radiation attenuation at an upcoming radiation source position or angular bin.

FIG. 5A plots dose modulated x-ray tube current versus table position for linear dose modulation techniques during a whole-body scan starting at the abdominal region and terminating in the head.

FIG. 5B plots dose modulated x-ray tube current versus table position for baseline-axial dose modulation techniques during a whole-body scan starting at the abdominal region and terminating in the head.

With reference to FIG. 1, a tomographic scanner 10 performs transmission tomographic imaging of an imaging subject (not shown) disposed in an imaging region 12. The scanner 10 includes a radiation source 14, such as an x-ray tube, disposed on a rotating gantry 16. As the gantry 16 rotates relative to a stationary frame 18, the radiation source 14 revolves about the imaging subject disposed in the imaging region 12. Transmission tomographic imaging data are acquired by detecting radiation in a detector region 20 disposed on the opposite side of the imaging region 12 from the radiation source 14. In the preferred embodiment, the radiation is detected by a radiation detector disposed on the rotating gantry 16 across the imaging region 12 from the radiation source 14. In other embodiments, an annular detector array is disposed on the stationary frame 18, and that portion of the annular detector array disposed across the imaging region 12 from the radiation source 14 during a given measurement is used for acquiring the transmission tomographic imaging data.

The imaging subject is moved into the imaging region 12 on a subject or patient couch 24 or other support. In axial imaging, the couch 24 remains stationary during acquisition of tomographic imaging data. Preferably, a plurality of rows of radiation detectors are disposed in the detector region 20, spaced along the axial or z-direction, to enable multi-slice imaging in which a plurality of spaced apart axial slices are acquired for each revolution of the radiation source 14. In helical imaging, the couch moves linearly during acquisition of tomographic imaging data in a direction that is substantially transverse to the plane of revolution of the radiation source 14, such that the radiation source 14 follows a helical trajectory respective to the imaging subject. Such helical imaging can be done with the direction of couch motion transverse to the plane of revolution or, in tilted helical imaging, can be done with a selected relative tilt between the direction of couch motion and the plane of revolution of the radiation source 14. Typically, for multi-slice or helical imaging the radiation source 14 produces a wedge-shaped, cone-shaped, or otherwise divergent or spread-out beam of radiation that is measured by a two-dimensional array of radiation detectors disposed in the detector region 20.

The above-described computed tomography scanner 10 is an illustrative example. The methods and apparatuses for dose modulation disclosed herein are readily applied in conjunction with substantially any type of transmission tomographic imaging technique. Moreover, the methods and apparatuses for dose modulation disclosed herein are also adaptable for dose modulation or dose regulation in transmission radiation therapy techniques in which the treatment radiation source revolves around the patient during therapy.

With continuing reference to FIG. 1, tomographic imaging data is acquired while the radiation source 14 revolves around the imaging region 12. The tomographic data is stored in a tomographic imaging data memory 30. In some embodiments, the transmission tomographic imaging data is logged as detector signal values $D_i$ given by:

$$D_i = -N \cdot \log_2(k \cdot P_{detector}) \tag{1}$$

where $P_{detector}$ corresponds to the radiation intensity at the detector element, and N and k are system constants of data acquisition. The x-ray transmission depends both on the detector signal $D_i$ and the input radiation intensity produced by the radiation source 14, denoted herein as $P_{source}$. A tomographic signal denoted "sig" is thus suitably defined as:

$$sig = -N \cdot \log_2(k \cdot P_{detector}) + N \log_2(k \cdot P_{source}) \tag{2}$$

values of which are stored in the imaging data memory 30. The imaging data are suitably reconstructed by a reconstruction processor 32, using for example a filtered backprojection reconstruction algorithm, to generate reconstructed images that are stored in a reconstructed images memory 34. The reconstructed images are displayed on a monitor 38 of a user interface 36, are electronically or magnetically stored, are transmitted over a local area network or the Internet, subjected to post-acquisition image processing, or are otherwise utilized. In some embodiments, the user interface 36 also enables the user to communicate with a tomographic controller 40 to control operation of the computed tomography scanner 10. In other embodiments, different user interfaces are used for displaying images and for controlling the scanner 10.

The tomographic controller 40 includes a dose modulation processor 42 that communicates with a radiation source power supply 44 to control the radiation intensity generated by the radiation source 14 during tomographic imaging. In the illustrated embodiment, the radiation source 14 is an x-ray tube, the power supply 44 is an x-ray tube power supply, and the dose modulation processor 42 controls the x-ray tube filament or cathode current to modulate the x-ray intensity generated by the x-ray tube 14. In other contemplated embodiments, dose modulation is produced by shuttering the radiation beam, by modulating the electrical bias on a Wehnelt cylinder, or so forth.

The dose modulation generally reduces the radiation intensity generated by the radiation source 14 when acquiring tomographic imaging data in a region exhibiting low attenuation of radiation. The dose modulation generally increases the radiation intensity generated by the radiation source 14 when acquiring tomographic imaging data in a region exhibiting high attenuation of radiation. More specifically, the dose is adjusted in accordance with the angular position of the x-ray tube around the subject. Dose modulation has advantages such as reducing the radiation exposure of the imaging subject and maintaining an appropriate signal level at the radiation detector to optimize image quality.

The dose modulation processor 42 adjusts the level of radiation produced by the radiation source 14 based on the radiation attenuation of previously acquired transmission tomographic imaging data. In this manner, the dose is varied by the longitudinal or z-position of the x-ray source, as well as its angular position. Toward this end, an attenuation processor 50 determines a measured attenuation for acquired positions of the radiation source 14 as it revolves around the imaging subject, based on the acquired transmission tomographic imaging data. In general, the attenuation is defined as the radiation input intensity at the source 14 divided by the transmitted intensity measured at the detector region 20. The intensity at the detector region 20 is attenuated respective to the intensity at the radiation source 14 by absorption, scattering, or other radiation loss mechanisms occurring during radiation transit through the imaging region 12. Referring back to Equation (2), dividing both sides by the number of measurements per revolution (N) of the radiation source and using the mathematical identity log(x/y)=log(x)–log(y) yields:

$$\frac{sig}{N} = \log_2\left(\frac{P_{source}}{P_{detector}}\right) = \log_2(A_i), \tag{3}$$

and $$A_i = \frac{P_{source}}{P_{detector}} = 2^{sig/N}, \tag{4}$$

where $A_i$ is the measured attenuation at a position indexed "i", or a processed result of attenuations at an angularly contiguous bin of several positions of the radiation source 14 collectively indexed "i". The attenuation values for each acquired position of the radiation source 14 are stored in an attenuations data memory 52 as the imaging scan progresses.

Equation (4) relates the attenuation $A_i$ to the example measured transmission tomographic signal "sig" stored in the tomographic imaging data memory 30. In other tomographic scanners, the measured transmission tomographic imaging data may be stored in a format other than that expressed in Equation (2). Those skilled in the art can readily derive expressions analogous to Equation (4) for determining the attenuation $A_i$ from measured transmission tomographic imaging data stored in other formats.

The current response of x-ray tube is usually slow, thus the attenuation $A_i$ that used to modulate tube current may be a processed result of attenuations at an angularly contiguous bin of several positions of radiation source 14 collectively indexed "i". Moreover, it will be appreciated that in the case of a cone beam or other radiation beam irradiating a two-dimensional multi-row detector disposed at the detector region 20, the attenuation $A_i$ is preferably computed from the detector row that is near the leading edge towards the scan direction as a maximum attenuation or other statistical characteristic attenuation value. In another embodiment the attenuation $A_i$ is calculated as a maximum after smoothing attenuations taken over the detector elements of the two-dimensional detector array with the radiation source 14 at the position indexed "i". Such smoothing or the like is further optionally weighted to emphasize detector elements near the most attenuated area of the detector array in determining the attenuations that are used to compute tube currents.

The dose modulation proceeds as follows. For each upcoming position of the radiation detector 14 at which transmission tomographic imaging data will be acquired, an estimate is made of the attenuation of radiation that will be encountered at that upcoming position. This estimate is made based on attenuation values of previously measured positions of the radiation source 14 which are stored in the attenuations data memory 52.

With reference to FIG. 2, one suitable approach for estimating the attenuation of radiation is described. FIG. 2 depicts a trajectory 60 of one revolution of the radiation source 14 around the region of interest 12. A center of the region of interest 12 is indicated by crosshairs 62. In the illustrated trajectory 60, the radiation source 14 moves in the direction indicated by arrow 64. Transmission tomographic imaging data are acquired at selected positions of the radiation source 14 along the trajectory 60. In FIG. 2, positions at which transmission tomographic imaging data have already been acquired are indicated by filled circles 70, while positions at which transmission tomographic imaging data are yet to be acquired are indicated by open circles 72.

For illustrative purposes, about fifty positions 70, 72 per revolution are illustrated in FIG. 2. However, it is to be understood that tomographic imaging scanners typically acquire tomographic imaging data at hundreds or thousands of angular positions of the radiation source per revolution of the radiation source. For example, the scans shown herein in FIGS. 3 and 5 employed tomographic imaging data acquisitions at 1160 angular positions per revolution, which for a typical gantry rotation rate of 120 revolutions per minute corresponds to one acquisition position every 0.43 milliseconds. However, the modulated tube current calculation is at lower rate because the current response of x-ray tube is much slower.

Accordingly, in some embodiments the positions 70, 72 for dose modulation have a lower angular resolution than the acquisition positions. For example, the positions 70, 72 may represent angular bins each containing a plurality of tomographic data acquisition positions. An estimated attenuation and x-ray current is determined for each angular bin and is employed all the acquisition positions in that bin. In some embodiments, angular bins each spanning three degrees are used; however, the angular span of each angular bin is generally selected based on the data processing speed, x-ray tube response, gantry rotation rate, and other factors. An attenuation for an upcoming bin is estimated based on the attenuation values measured for one or more of the acquisition positions within a previously acquired bin, for example the bin located a half-revolution before the upcoming bin. Alternately, the attenuation from the same bin but one revolution preceding can be used. A modulated x-ray tube current is computed for that estimated attenuation and is used for all the measurement positions contained within the upcoming bin. The estimated attenuation can be, for example, an attenuation of a central acquisition position within the bin, or can be an average, maximum, or other statistical characteristic attenuation averaged over all the acquisitions positions contained within the previously measured bin. The positions 70, 72 of the radiation source refer to either tomographic data acquisition positions or, in a binned dose modulation approach, to angularly contiguous bins each containing a plurality of tomographic data acquisition positions having a common dose modulation level.

For expository purposes, a position or angular bin $72_1$ of the radiation source 14 is identified in FIG. 2. The position or bin $72_1$ is upcoming for acquisition of transmission tomographic imaging data. The attenuation of radiation for data acquisition at upcoming position $72_1$ is in this approach suitably estimated based on the attenuation of radiation obtained from a previously acquired position or bin located about a half-rotation away from the upcoming position or bin $72_1$. This previously acquired position or bin is identified as $70_1$ in FIG. 2. Because this previously acquired position $70_1$ is about 180° away from the upcoming position $72_1$, the radial direction of the transmission path for position $70_1$ is about parallel to the transmission path for position $72_1$. In the case of helical computed tomography, the radiation paths of the positions $70_1$, $72_1$ are offset by about one-half of the helical pitch. For small or modest helical pitches, attenuation at the previously acquired 180° opposite position or bin $70_1$ generally provides a good estimate of the attenuation that will be encountered when acquiring tomographic imaging data at the upcoming position or bin $72_1$.

To perform the dose modulation at the position $72_1$, the estimated attenuation $A_i$ at the position $72_1$ is estimated as the attenuation at the previously acquired position $70_1$, which is recalled from the attenuations data memory 52. This estimated attenuation $A_i$ is used to determine an appropriate level of radiation output from the radiation source 14 for use in acquiring transmission tomographic imaging data at the upcoming position $72_1$. In general, a larger attenuation $A_i$ calls for a higher level of radiation output from the radiation source 14. In embodiments in which the radiation source 14 is an x-ray tube, the radiation output is suitably controlled by modulating the x-ray tube current, denoted $I_i$ herein for the position or angular bin indexed "i", that is, for the upcoming position $72_1$ in the illustrated example. In one approach, the x-ray current is adjusted based upon the estimated attenuation $A_i$ raised to a selected power factor $\alpha$:

$$I_i \propto (A_i)^\alpha \tag{5}$$

In some embodiments, a value of $\alpha=0.5$ corresponding to a square-root relationship:

$$I_i \propto \sqrt{A_i} \tag{6}$$

is used. This value of $\alpha$ has been found to be suitable for two-dimensional axial dose modulation in some x-ray tomographic systems (see, e.g., Gies et al., Med. Phys. 26(11), pp.

2235-47 (1999)) and provides an optimized current modulation. However, in many cases the power of the x-ray tube and the response of the tube current limit the amplitude of the current modulation and cannot support larger $\alpha$. More generally, the power factor $\alpha$ should be between about 0.1 and about 0.5 depending upon the scanner system and applications.

In one approach for determining x-ray tube currents, a unit current $I_{unit}$ that corresponds to a selected image noise level or image quality of the first revolution of the scan is calculated. During the initial revolution the x-ray tube current is held constant at a nominal value $I_{nom}$ that is determined by the scan protocol or selected by the clinician to ensure a satisfactory image quality. An average attenuation raised to the a power for this first revolution of the radiation source is denoted $|A^\alpha|_{initial}$ where $|\cdot|$ denotes an average, mean, or other statistical characteristic attenuation computed over the initial revolution. A maximum attenuation raised to the power $\alpha$ in the first revolution is designated $\max\{A^\alpha\}_{initial}$. An optimized mean x-ray tube current for the initial revolution, denoted $|I|_{initial}$, is given as:

$$|I|_{initial} = \frac{|A^\alpha|_{initial}}{\max\{A^\alpha\}_{initial}} \cdot I_{nom}. \qquad (7)$$

The current proportionality factor $I_{unit}$ is then determined as:

$$I_{unit} = \frac{|I|_{initial}}{|A^\alpha|_{initial}} = \frac{I_{nom}}{\max\{A^\alpha\}_{initial}}. \qquad (8)$$

Using the determined unit current $I_{unit}$, the proportionality Equation (5) can be rewritten as an equality:

$$I_i = I_{unit} \cdot (A_i)^\alpha \qquad (9),$$

where $A_i$ is the estimated attenuation for the position or angular bin indexed "i". Optionally, clamping or limiting values for the x-ray tube current are also defined. For example, a maximum current $I_{high}$ can be given by:

$$I_{high} = \min\{1.3 \cdot I_{nom}, 500 \text{ mA}\} \qquad (10),$$

and a minimum current $I_{low}$ can be given by:

$$I_{low} = \max\{0.3 \cdot I_{nom}, 50 \text{ mA}\} \qquad (11).$$

Equations (5)-(11) are suitable for dose modulation performed through modulation of an x-ray tube current. Preferably, the change in x-ray tube current is made slightly in advance of the tube reaching the position in question to account fox thermal inertia of the filament, generator RC time constant, and so on. The change in filament temperature is not instantaneous with filament current change. Rather, a short period of time is needed to heat or cool the filament. The exact timing is determined by the x-ray tube and generator characteristics, and the rotation speed. In other embodiments, other mechanisms for dose modulation may be used. For example, a shutter can be oscillated to block the radiation beam during a portion of the time. In this case, the duty cycle of the shuttered beam determines the effective or average radiation source power $P_{source}$. In this case, a suitable relationship can be determined between duty cycle and attenuation $A_i$ to provide the desired correspondence between the effective or average radiation source power $P_{source}$ and the attenuation $A_i$.

With reference to FIG. 3A, results for a whole-body helical tomographic scan are illustrated. The top graph of FIG. 3A plots the tomographic signal "sig" given in Equation (2) plotted against position of the table 24. The table position corresponds to a linear coordinate in the z-direction. The "sig" data is readily converted to attenuation data through Equation (4). The "sig" plot is generally periodic, with the distance between each pair of adjacent peaks corresponding to a one-half revolution of the radiation source 14. This periodicity results from the variations in human body density as a function of angular position of the radiation source 14. The "sig" plot further exhibits a lower frequency variation along the z-direction due to variations in human body density in the z-direction. In this regard, regions of the body including the "Head+arm", "Neck+arm", "Shoulder", "Chest", and "Abdomen" are labeled on the "sig" plot. The neck region, in particular, is seen to have lower average "sig" (and correspondingly lower average radiation attenuation) as compared with the other regions. The half-revolution periodicity of the "sig" data (and, correspondingly, of the attenuation) coupled with the generally low frequency variation in density in the z-direction justifies estimating the attenuation for an upcoming position or angular bin based on an attenuation determined from tomographic imaging data previously acquired at a position or bin about 180° away.

The bottom graph of FIG. 3B plots the dose-modulated x-ray tube current against table position for the whole-body helical scan. The dose modulation was performed using the linear method of Equations (4) and (7)-(11), where $I_{nom}$ was selected to be 240 milliamperes and $\alpha=0.2$. The dose modulation was performed using position bins each spanning three angular degrees of revolution of the radiation source 14. In an initial region 76, the initial calibration revolution of the radiation source was performed, during which the x-ray tube current was maintained constant at $I_{nom}=240$ milliamperes. The remainder is dose modulated based on the calibrated values, and is seen to closely track both the high frequency (that is, half-revolution periodicity) and low frequency components of the "sig" plot.

With returning reference to FIG. 1 and further reference to FIG. 4, in helical tomographic imaging the table 24 moves simultaneously with revolving of the radiation source 14, producing a helical trajectory 80. In FIG. 4, arrows along the trajectory 80 indicate the direction in which the radiation source 14 moves. The helical trajectory 80 has a helical pitch, labeled "P" in FIG. 4. The pitch "P" has a length of about the distance traveled by the table 24 during one revolution of the radiation source 14. (For tilted gantry helical tomographic imaging, the effective pitch may be slightly affected by the relative tilt between the plane of revolution of the radiation source and the direction of table motion).

In FIG. 4, an upcoming radiation source position or angular bin 82 which is about to be acquired is indicated by an open circle. A previously acquired position or bin 84 located a half-revolution away from the upcoming position or bin 82 is indicated by a filled circle. In addition to being angularly separated by a 180° half-rotation of the radiation source 14, the positions or bins 82, 84 are separated along the z-direction by a distance of one-half of the pitch "P". Because of the typically low frequency modulation of imaging subject density along the z-direction, however, this small z-direction separation due to the pitch typically corresponds to a small change in attenuation, and so the attenuation determined from the tomographic imaging data acquired at the position or bin 82 is a suitable estimate of the attenuation which is expected to be encountered when acquiring tomographic imaging data at the upcoming position or bin 84. (It is to be appreciated that the helical trajectory 80 shown in FIG. 4 is diagrammatic, and is stretched out in the z-direction to illustrate features including the pitch "P" and the separation of the positions or bins 82, 84 along the z-direction. Typically, the helical pitch "P" has a length of a few centimeters or less, while the span between the radiation source 14 and the detector region 20 is usually more than 100 centimeters across).

With continuing reference to FIG. 4, another approach for determining an estimated attenuation of radiation at the upcoming radiation source position or angular bin 82 is described. In this approach, the modulated x-ray tube current $I_i$ includes a baseline contribution and an axial contribution. The baseline contribution is determined from an average or other statistical characteristic baseline attenuation encountered over an extended angular range of measurement. For example, in FIG. 4, the baseline tube current is determined from attenuation averaged over a full revolution 90 (indicated by a thicker curve in FIG. 4) of the radiation source 14 acquired prior to the tomographic data acquisition at the upcoming position or bin 84. This attenuation averaged over the revolution 90 approximately corresponds to an average attenuation encountered when acquiring imaging data from a cylindrical portion 92 of the imaging region 12. In some embodiments, the baseline tube current contribution $I_{i,baseline}$ is computed as:

$$I_{i,baseline} = \frac{|(A_i)^\alpha|}{|(A)^\alpha|_{initial}} \cdot |I|_{initial}, \quad (12)$$

where $|(A_i)^\alpha|$ is the attenuation raised the $\alpha$ power averaged over the revolution 90, $|I|_{initial}$ is set forth in Equation (7), and $|(A_i)^\alpha|_{initial}$ is the attenuation raised to the $\alpha$ power averaged over the first revolution.

In some embodiments, the axial contribution to the modulated tube current, denoted herein as $I_{i,axial}$, is computed from an estimated attenuation $A_i$ determined from tomographic imaging data previously acquired at the previous position or bin 84 a half-rotation away from the upcoming position or bin 82. For example, the axial contribution $I_{i,axial}$ is in some embodiments suitably given by:

$$I_{i,axial} = \left( \frac{(A_i)^\alpha}{\max\{(A_i)^\alpha\}} - \frac{|(A_i)^\alpha|}{\max\{(A_i)^\alpha\}} \right) \cdot I_{nom}. \quad (13)$$

The total x-ray tube current $I_i$ is computed as the sum of Equations (12) and (13). Optionally, the total current $I_i$ is limited or clamped by suitable limits such as the $I_{high}$ and $I_{low}$ limits set forth in Equations (10) and (11), respectively. In the dose modulation method of Equations (12) and (13), the baseline contribution $I_{i,baseline}$ tracks the typically low frequency attenuation component corresponding to gradual variation of imaging subject density along the z-direction, while the axial contribution $I_{i,axial}$ tracks the typically higher frequency attenuation component due to the half-rotation periodicity introduced by revolving of the radiation source 14.

With reference to FIGS. 5A and 5B, dose modulation using the method of Equations (7)-(9), shown in FIG. 5A, is compared with dose modulation using the method of Equations (12) and (13), shown in FIG. 5B. These plots show dose modulated x-ray tube current versus table position for helical scans of a human body starting in the abdominal region and terminating at the head. In both scans, the nominal current $I_{nom}$ for the first calibration rotation was 300 milliamperes. Both the linear dose modulation of Equations (7)-(9) (upper graph) and the baseline-axial dose modulation of Equations (12) and (13) employed $\alpha$=0.2. Comparison of the two dose modulation plots show that the two methods produce substantially similar dose micromodulation results.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

The invention claimed is:

1. A method of dose modulation in CT imaging comprising:
    acquiring initial transmission tomographic imaging data of an associated imaging subject using an x-ray radiation source revolving around the associated imaging subject for an initial revolution of the radiation source using a preselected level of radiation generated by the x-ray radiation source;
    estimating a constant of proportionality relating:
    (i) x-ray current of the x-ray radiation source and
    (ii) attenuation of radiation raised to a selected power, the constant of proportionality being estimated based on the initial transmission tomographic imaging data acquired in the initial revolution;
    performing tomographic imaging by acquiring transmission tomographic imaging data of the associated imaging subject using the x-ray radiation source revolving around the associated imaging subject;
    during the tomographic imaging, determining an estimated attenuation of radiation for an upcoming position or angular bin of the revolving radiation source based on attenuations measured at previous positions or angular bins of the x-ray radiation source; and
    prior to acquiring tomographic imaging data at the upcoming position or angular bin, adjusting a level of radiation produced by the x-ray radiation source by adjusting the x-ray current proportional to the estimated attenuation of radiation for the upcoming position or angular bin raised to the selected power using the estimated constant of proportionality.

2. The dose modulation method according to claim 1, wherein the determining of an estimated attenuation of radiation includes:
    estimating the attenuation based on attenuations measured for a previously acquired position or angular bin in which the radiation source was about an integer multiple of a half revolution away from the upcoming position or angular bin.

3. The dose modulation method as set forth in claim 2, wherein the acquiring of tomographic imaging data includes:
    relatively moving the associated imaging subject and the radiation source in a longitudinal direction generally transverse to a plane of revolution of the radiation source such that the radiation source follows a generally helical trajectory respective to the associated imaging subject.

4. The dose modulation method as set forth in claim 1, wherein the adjusting of an x-ray current includes:
    limiting the adjusting of the x-ray current to a range defined by a minimum current value and a maximum current value.

5. The dose modulation method as set forth in claim 1, wherein the adjusting of the x-ray current proportional to the estimated attenuation of radiation raised to the selected power using the estimated constant of proportionality comprises:
adjusting the x-ray current proportional to a square root of the estimated attenuation of radiation using the estimated constant of proportionality.

6. The dose modulation method as set forth in claim 1, wherein the selected power is between about 0.1 and about 0.5.

7. A dose modulation processor for performing the dose modulation method set forth in claim 1.

8. A method of dose modulation method in CT imaging, the method comprising:
acquiring transmission tomographic imaging data of an associated imaging subject using a radiation source revolving around the associated imaging subject;
during the tomographic imaging, determining an estimated attenuation of radiation for an upcoming position or angular bin of the revolving radiation source based on attenuations measured at previous positions or angular bins of the radiation source, the determining including (i) estimating a baseline radiation attenuation based on an average attenuation over an extended range of positions preceding the upcoming position or angular bin and (ii) estimating an axial radiation attenuation based on a previously acquired position or angular bin of the radiation source disposed about a half revolution away from the upcoming position; and
prior to acquiring tomographic imaging data at the upcoming position or angular bin, adjusting a level of radiation produced by the radiation source based on the estimated attenuation of radiation by (i) determining a baseline x-ray current component based on a ratio of the estimated baseline attenuation of the upcoming position or angular bin and the average attenuation of the initial revolution, (ii) determining an axial x-ray current component based on a ratio of the estimated axial attenuation of the upcoming position or angular bin and a maximum or average attenuation of a present revolution, and (iii) determining a total x-ray current by combining the baseline and axial x-ray current components.

9. A CT scanner including a processor programmed to perform a method according to claim 8.

10. The dose modulation method as set forth in claim 8, wherein the acquiring of tomographic imaging data includes:
acquiring helical tomographic imaging data.

11. The method of claim 10, further comprising:
during the acquiring, revolving the radiation source around the associated imaging subject and simultaneously linearly moving the associated imaging subject such that the revolving and linear moving cooperatively define a helical orbit of the radiation source relative to the associated imaging subject.

12. The dose modulation method as set forth in claim 8, wherein the estimating of a baseline modulation attenuation includes:
estimating the baseline modulation attenuation based on an average attenuation of transmission tomographic imaging data spanning an integer multiple of a revolution of the radiation source.

\* \* \* \* \*